(12) United States Patent
Gerke et al.

(10) Patent No.: US 8,604,250 B2
(45) Date of Patent: Dec. 10, 2013

(54) PHOTOLABILE PRO-FRAGRANCES

(75) Inventors: Thomas Gerke, Duesseldorf (DE); Christian Kropf, Hilden (DE); Ursula Huchel, Cologne (DE); Axel Griesbeck, Cologne (DE); Olga Hinze, Cologne (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/584,977

(22) Filed: Aug. 14, 2012

(65) Prior Publication Data

US 2012/0315403 A1    Dec. 13, 2012

Related U.S. Application Data

(63) Continuation of application No. PCT/EP2011/050243, filed on Jan. 11, 2011.

(30) Foreign Application Priority Data

Feb. 17, 2010    (DE) .......................... 10 2010 002 006

(51) Int. Cl.
  *C07C 49/798*    (2006.01)
  *C11D 3/50*      (2006.01)
  *B05D 5/00*      (2006.01)

(52) U.S. Cl.
  USPC .............. 568/329; 512/21; 510/106; 427/558

(58) Field of Classification Search
  USPC .............. 568/329; 512/21; 510/106; 427/558
  See application file for complete search history.

(56) References Cited

U.S. PATENT DOCUMENTS

| | | |
|---|---|---|
| 6,949,680 B2 | 9/2005 | Herrmann |
| 2007/0264217 A1 | 11/2007 | Dykstra et al. |

FOREIGN PATENT DOCUMENTS

| | | |
|---|---|---|
| SU | 717031 A1 | 2/1980 |
| WO | 2007/087977 A1 | 8/2007 |
| WO | 2009/118219 A1 | 10/2009 |

OTHER PUBLICATIONS

Dell'Erba et al, "a-Arylation vs. a-Arylhydrazonylation of Alkyl Aryl Ketones with Arylazo tert-Butyl Sulfides", Tetrahedron, 1993, vol. 49, No. 1, pp. 235-242.
Kobayashi et al, "Novel Reactive Silyl Enolates. Highly Stereoselective Aldol and Michael Reactions without Catalysts", Journal of Organic Chemistry, 1993, vol. 58, No. 10, pp. 2647-2649.
Heathcock et al, "Stereoselection in the Michael Addition Reaction. 1. The Mokaiyama-Michael Reaction", Journal of the American Chemical Society, 1985, vol. 107, No. 9, pp. 2797-2799.
Bensa et al, "P-BEMP: A New Efficient and Commercially Available User-Friendly and Recyclable Heterogeneous Organocatalyst for the Michael Addition of 1,3-Dicarbonyl Compounds", Synthesis, 2004, No. 6, pp. 923-927.
Jiang et al, "Synthesis of a-Stereogenic Amides and Ketones by Enantioselective Conjugate Addition of 1,4-Dicarbonyl But-2-enes", Chemistry a European Journal, 2009, vol. 15, pp. 4925-4930.
PCT International Search Report (PCT/EP2011/050243) dated Jul. 25, 2011.

*Primary Examiner* — Sikarl Witherspoon
(74) *Attorney, Agent, or Firm* — Thomas G. Krivulka

(57) ABSTRACT

Scents having a fresh odor are usually very volatile, and therefore have a low yield in typical applications such as washing or cleaning processes. They must therefore be used in relatively large quantities so that commensurate effects can be achieved. The invention describes specific ketones as photolabile scent storage substances which enable greatly improved persistence of the scent impression, in particular with a fresh odor, in typical applications. Corresponding washing or cleaning agents and air freshening agents, and a method for scenting surfaces, are also described.

10 Claims, No Drawings

PHOTOLABILE PRO-FRAGRANCES

CROSS-REFERENCES TO RELATED APPLICATIONS

This application is a continuation of PCT/EP2011/050243, filed on Jan. 11, 2011, which claims priority under 35 U.S.C. §119 to DE 10 2010 002 006.0 filed on Feb. 17, 2010, both of which are hereby incorporated by reference.

FIELD OF THE INVENTION

The present invention generally relates to scent storage substances, such as those used, for example, in the sector of washing or cleaning agents, cosmetic agents, or air freshening agents, and more particularly relates to special ketones that function as photolabile scent storage substances. The present invention further relates to washing or cleaning agents, cosmetic agents, and air freshening agents that contain such ketones. It further relates to a method for long-lasting scenting of surfaces, and also to a method for long-lasting room scenting.

BACKGROUND OF THE INVENTION

Washing or cleaning agents resp. cosmetic agents usually contain scents that impart a pleasant odor to the agents. The scents usually mask the odor of the other ingredients, producing a positive odor impression on the consumer.

In the sector of washing agents in particular, scents are important constituents of the composition, since the laundry should have a pleasant and, if possible, also fresh smell both when wet and when dry. A fundamental problem faced in the utilization of scents is that these are more or less volatile substances, but that a long-lasting scent effect is nevertheless desirable. The desired persistence of the scent impression is very difficult to achieve especially with those fragrances that represent the flesh and light notes of the perfume, and that evaporate particularly quickly because of their high vapor pressure.

Delayed scent release can occur, for example, thanks to carrier-bound use of scents. A carrier-bound precursor form of a scent is also known as a "pro-fragrance" or scent storage substance. In this connection, International Patent Application WO 2007/087977 discloses the use of 1-aza-3,7-dioxabicyclo[3.3.0]octane compounds as scent storage substances for delayed release of scent aldehydes and scent ketones by hydrolysis. An alternative possibility for delayed release of scents is represented by the use of so-called photoactivatable substances as scent storage substances. The action of sunlight or another electromagnetic radiation source of a specific wavelength induces breakage of a covalent bond in the scent storage substance molecule, thereby releasing a scent.

U.S. Pat. No. 6,949,680 discloses the use of specific phenyl ketones or pyridyl ketones as photoactivatable substances that, in a photochemical fragmentation, release a terminal alkene as an active substance in the presence of light. The aforesaid active substance possesses, for example, a scent-imparting or antimicrobial activity that is first delayed by the photochemically induced decomposition, and over a longer period of time is released on a specific surface. WO 2009/118219 A1 discloses photoactivatable substances that permit the release of cyclic terpenes or cyclic terpenoids.

The object of the present invention was to provide photo-activatable substances constituting scent storage substances, which permit the delayed release of fragrance ketones, in particular damascones.

This object is achieved by a ketone of the general formula (I)

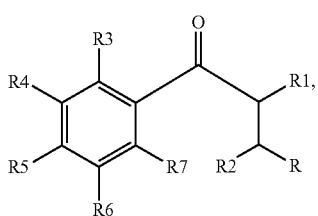

Formula (I)

in which
R denotes a hydrocarbon residue that comprises at least one C=O group,
R1 denotes a linear or branched, substituted or unsubstituted alkyl group having 1 to 6 carbon atoms, in particular a methyl group,
R2, R3, R4, R5, R6, and R7, mutually independently, denote hydrogen, a halogen atom, $NO_2$, a linear or branched, substituted or unsubstituted alkoxy group having 1 to 15 carbon atoms or a linear or branched, substituted or unsubstituted alkyl group having 1 to 15 carbon atoms.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A ketone of the general formula (I)

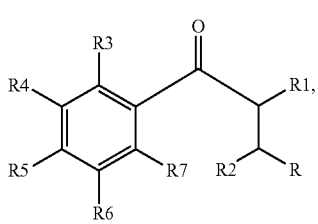

Formula (I)

in which R denotes a hydrocarbon residue that comprises at least one C=O group; R1 denotes a linear or branched, substituted or unsubstituted alkyl group having 1 to 6 carbon atoms; R2, R3, R4, R5, R6, and R7, mutually independently, denote hydrogen, a halogen atom, $NO_2$, a linear or branched, substituted or unsubstituted alkoxy group having 1 to 15 carbon atoms or a linear or branched, substituted or unsubstituted alkyl group having 1 to 15 carbon atoms.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has been found, surprisingly, that the ketones according to the present invention are particularly effective scent storage substances that permit the delayed release of fragrance ketones, in particular damascones. Use of the ketones according to the present invention in washing, cleaning, or care-providing agents resulted, in the context of their utilization, in an improved long-term scent effect, in particular in conjunction with textile treatment. For example, with the use of ketones according to the present invention in a laundry treatment agent, for example a washing agent and a fabric softener, it was possible to observe an improved long-term scent effect in the treated laundry. In addition, corresponding products exhibit particularly good shelf stability. The agents according to the present invention further make it possible to reduce the total quantity of perfume contained in the agent, but nevertheless to achieve odor advantages on the washed textiles, in particular with regard to perceived freshness.

The ketone according to the present invention in accordance with the general formula (I) is suitable as a scent storage substance for all usual scent ketones, selected in particular from buccoxime; isojasmone; methyl-beta-naphthyl ketone; musk indanone; Tonalide/Musk Plus; alpha-damascone, beta-damascone, delta-damascone, gamma-damascone, damascenone, damarose, methyldihydrojasmonate, menthone, carvone, camphor, fenchone, alpha-ionone, beta-ionone, gamma-methyl (so-called) ionone, fleuramone, dihydrojasmone, cis-jasmone, iso-E-Super®, methylcedrenyl ketone or methylcedrylone, acetophenone, methylacetophenone, para-methoxyacetophenone, methyl-beta-naphtyl ketone, benzylacetone, benzophenone, para-hydroxyphenylbutanone, celery ketone or livescone, 6-isopropyldecahydro-2-naphthone, dimethyloctenone, frescomenthe, 4-(1-ethoxyvinyl)-3,3,5,5-tetramethylcyclohexanone, methylheptenone, 2-(2-(4-methyl-3-cyclohexen-1-yl)propyl)cyclopentanone, 1-(p-menthen-6(2)yl)-1-propanone, 4-(4-hydroxy-3-methoxyphenyl)-2-butanone, 2-acetyl-3,3-dimethylnorbornane, 6,7-dihydro-1,1,2,3,3 -pentamethyl-4 (5H)indanone, 4-damascol, dulcinyl or cassione, gelsone, hexalone, isocyclemone E, methylcyclocitrone, methyllavender ketone, orivone, para-tertiary butylcyclohexanone, verdone, delphone, muscone, neobutenone, plicatone, veloutone, 2,4,4,7-tetramethyloct-6-en-3-one, tetrameran, or mixtures thereof. The ketones can preferably be selected from the damascones, carvone, gamma-methylionone, iso-E-Super, 2,4,4,7-tetramethyl-oct-6-en-3-one, benzylacetone, damascenone, methyldihydrojasmonate, methylcedrylone, hedione, and mixtures thereof. All damascones, as well as damascenones, are most preferred. The stored ketones can be released by the action of light encompassing the wavelengths from 200 to 400 nm.

According to a preferred embodiment of the invention, the substituent R2 in formula (I) denotes a linear or branched, substituted or unsubstituted alkyl group having 1 to 6 carbon atoms, by preference 1 to 3 carbon atoms, and in particular is a methyl residue.

According to a further preferred embodiment of the invention, the substituents R3, R4, R5, R6, and R7 in formula (I) denote hydrogen.

Also preferred is a ketone according to the present invention of the general formula (I) in which four of the five aryl substituents R3, R4, R5, R6, and R7 denote hydrogen. R3, R4, R6, and R7 by preference denote hydrogen, while the R5 substituent denotes a halogen atom, in particular —F, —Cl, or —Br, $NO_2$, a linear or branched, substituted or unsubstituted alkoxy group having 1 to 6 carbon atoms, or a linear or branched, substituted or unsubstituted alkyl group having 1 to 6 carbon atoms. In a greatly preferred embodiment of the invention, R5 in formula (I) denotes —Cl, —Br, $NO_2$, or an alkyl or alkoxy group encompassing 1 to 4 carbon atoms. R5 is by preference a methyl or ethyl group, or a methoxy, ethoxy, isopropoxy, or tert-butoxy group. A substitution in the para-position (R5) is particularly preferred because the electron structure of the aromatic ring can be most effectively modified here, with the result that the absorption maximum of ketones of the general formula (I) can easily be adapted to a specific wavelength.

It is very particularly preferred if in formula (I), the substituents R3, R6, R7 denote hydrogen, the residue R4 denotes hydrogen or an alkoxy group, in particular a methoxy group, and the residue R5 denotes an alkoxy group, in particular a methoxy group.

According to a preferred embodiment of the invention, ketones corresponding to the formulas (II), (III), (IV), or formula (V) below are particularly preferred:

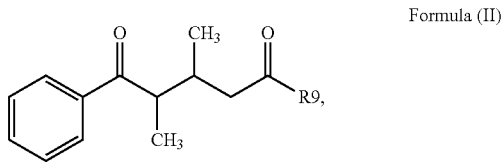

Formula (II)

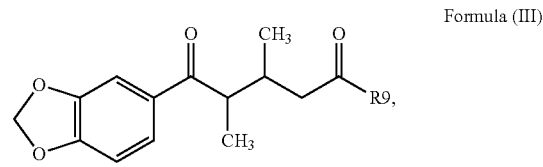

Formula (III)

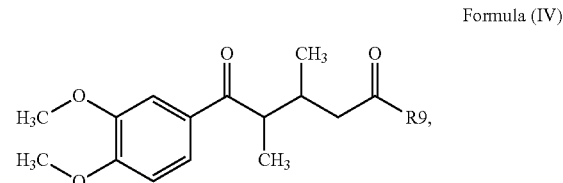

Formula (IV)

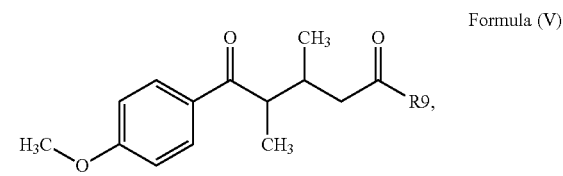

Formula (V)

where, in these formulas (II) to (V), the residue R9 denotes a hydrocarbon residue having at least 5 carbon atoms, which in particular encompasses a cyclic hydrocarbon residue.

According to a further preferred embodiment of the invention, ketones corresponding to formulas (VI) to (XXV) are preferred:

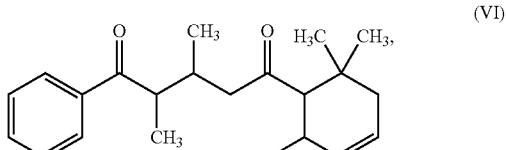

(VI)

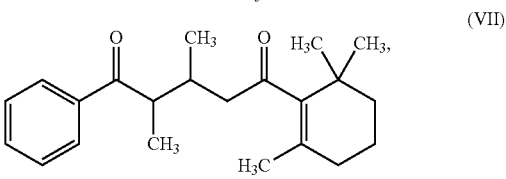

(VII)

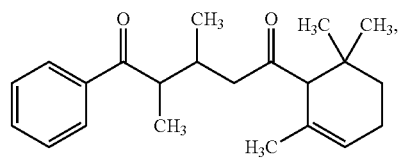
(VIII)
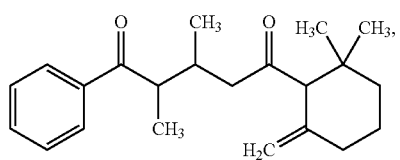
(IX)
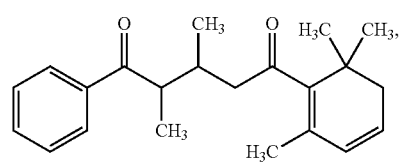
(X)
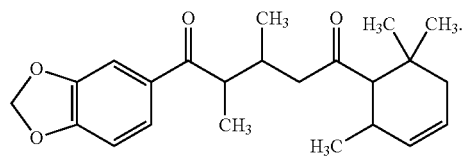
(XI)
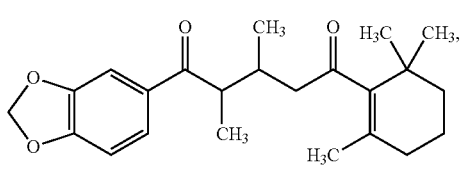
(XII)
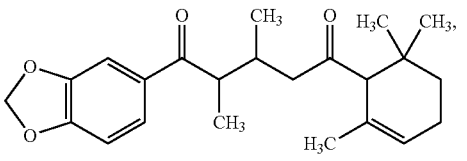
(XIII)
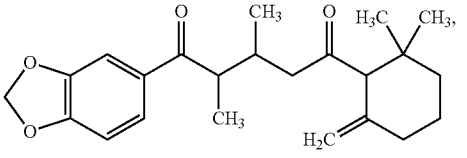
(XIV)
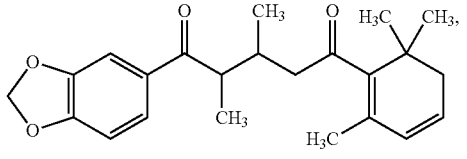
(XV)
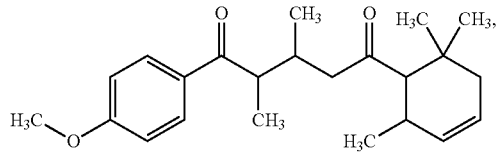
(XVI)
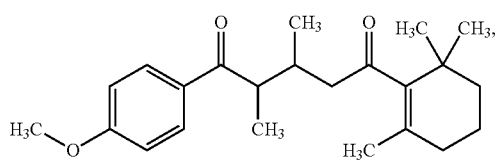
(XVII)
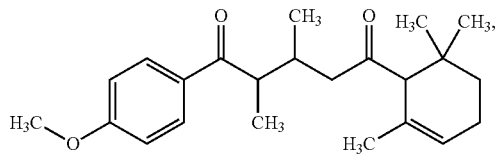
(XVIII)
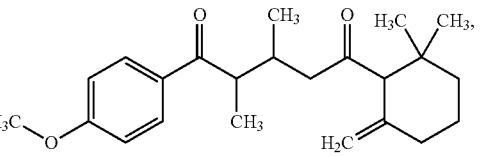
(XIX)
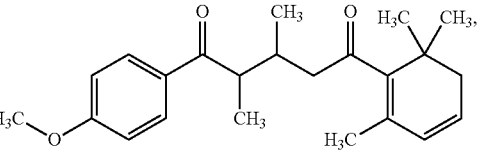
(XX)
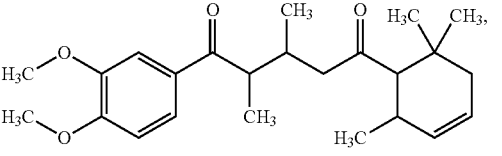
(XXI)
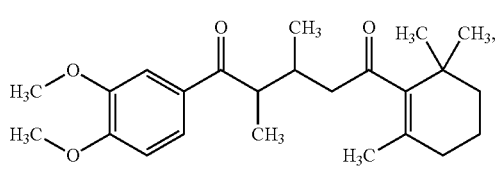
(XXII)
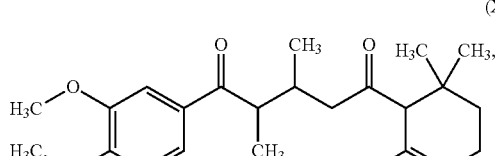
(XXIII)
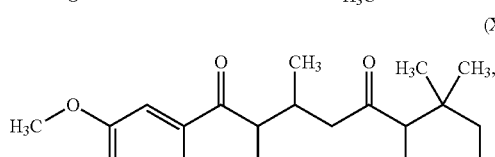
(XXIV)
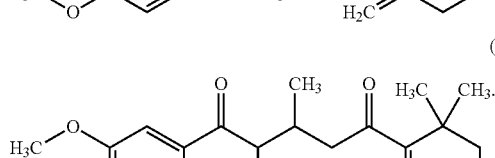
(XXV)

These ketones of formulas (VI) to (XXV) recited above can be incorporated in stable fashion into the usual washing- or cleaning-agent matrices, into cosmetics and existing fragrance compositions. They enable delayed release of the stored scents, namely of damascones in the α-, β-, or γ-, or Δ- form, and of damascenones, in particular β-damascenones. These ketones impart a particularly long-lasting fresh impression to usual washing or cleaning agents and cosmetics. The dried, washed textile profits in particular from the good long-term fresh scent effect. Slow release of the stored fragrance occurs after the action of light (electromagnetic radiation) encompassing the wavelengths from 200 to 400 nm, as illustrated in simplified fashion in the reaction equation below:

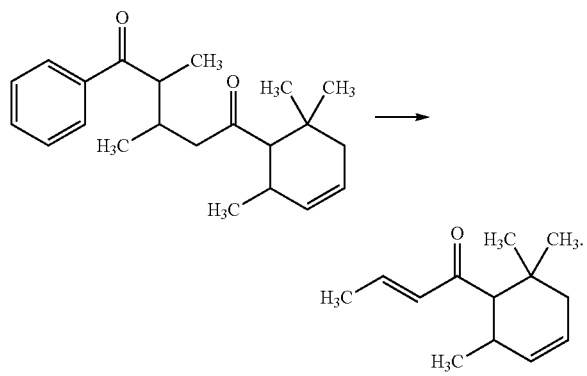

A further subject of the present invention is a washing or cleaning agent, by preference a washing agent, fabric softener, or washing adjuvant, containing at least one ketone in accordance with one of formulas (I) to (XXV), said ketone being contained by preference in quantities between 0.0001 and 5 wt %, advantageously between 0.001 and 4 wt %, more advantageously between 0.01 and 3 wt %, in particular between 0.1 and 2 wt %, based in each case on the total agent. Suitable cleaning agents are, for example cleaning agents for hard surfaces, such as by preference dishwashing agents. The cleaning agents can also, for example, be household cleaners, all-purpose cleaners, window cleaners, floor cleaners, etc. The product can by preference be one for cleaning toilet bowls and urinals, advantageously a toilet flush cleaner for suspension in the toilet bowl, in particular a so-called toilet block.

According to a preferred embodiment of the invention, the washing and/or cleaning agent according to the present invention contains at least one surfactant, selected from anionic, cationic, nonionic, zwitterionic, amphoteric surfactants or mixtures thereof.

According to a further preferred embodiment of the invention, the agent according to the present invention is present in solid or liquid form.

A further subject of the invention is a cosmetic agent containing at least one ketone in accordance with one of formulas (I) to (XXV), said ketone being contained by preference in quantities between 0.0001 and 5 wt %, advantageously between 0.001 and 4 wt %, more advantageously between 0.01 and 3 wt %, in particular between 0.1 and 2 wt %, based in each case on the total agent.

A further subject of the invention is an air freshening agent (e.g. room air freshener, room deodorant, room spray, etc.) containing at least one ketone in accordance with one of formulas (I) to (XXV), said ketone being contained by preference in quantities between 0.0001 and 50 wt %, advantageously between 0.001 and 5 wt %, more advantageously between 0.1 and 3 wt %, in particular between 0.1 and 2 wt %, based in each case on the total agent.

According to a further preferred embodiment of the invention, additional scents are contained in an agent according to the present invention (i.e. washing or cleaning agent, cosmetic agent, or air freshening agent), selected in particular from the group encompassing scents of natural or synthetic origin, preferably more-volatile scents, higher-boiling scents, solid scents, and/or adherent scents.

Adherent fragrances that are usable with advantage in the context of the present invention are, for example, essential oils such as angelica oil, anise oil, arnica flower oil, basil oil, bay oil, bergamot oil, champaca flower oil, silver fir oil, silver fir cone oil, elemi oil, eucalyptus oil, fennel oil, fir needle oil, galbanum oil, geranium oil, gingergrass oil, guaiac wood oil, balsam gurjun oil, helichrysum oil, ho oil, ginger oil, iris oil, cajeput oil, calamus oil, chamomile oil, camphor oil, kanaga oil, cardamom oil, cassia oil, pine needle oil, balsam copaiva oil, coriander oil, curled peppermint oil, caraway oil, cumin oil, lavender oil, lemon grass oil, lime oil, tangerine oil, lemon balm oil, ambrette seed oil, myrrh oil, clove oil, neroli oil, niaouli oil, olibanum oil, orange oil, oregano oil, palmarosa oil, patchouli oil, balsam peru oil, petitgrain oil, pepper oil, peppermint oil, pimento oil, pine oil, rose oil, rosemary oil, sandalwood oil, celery oil, spike lavender oil, star anise oil, turpentine oil, thuja oil, thyme oil, verbena oil, vetiver oil, juniper berry oil, wormwood oil, wintergreen oil, ylang-ylang oil, ysop oil, cinnamon oil, cinnamon leaf oil, citronella oil, lemon oil, and cypress oil.

Higher-boiling resp. solid fragrances of natural or synthetic origin can, however, also be used in the context of the present invention as adherent fragrances resp. fragrance mixtures, i.e. scents. These compounds include the compounds recited below, as well as mixtures thereof: ambrettolide, <-amylcinnamaldehyde, anethole, anisealdehyde, anise alcohol, anisole, anthranilic acid methyl ester, acetophenone, benzyl acetone, benzaldehyde, benzoic acid ethyl ester, benzophenone, benzyl alcohol, benzyl acetate, benzyl benzoate, benzyl formate, benzyl valerate, borneol, bornyl acetate, <-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrol, jasmone, camphor, carvacrol, carvone, p-cresol methyl ether, coumarin, p-methoxyacetophenone, methyl-n-amyl ketone, methylanthranilic acid methyl ester, p-methylacetophenone, methylchavicol, p-methylquinoline, methyl ®-naphthyl ketone, methyl-n-nonylacetaldehyde, methyl-n-nonyl ketone, muscone, ®-naphthol ethyl ether, ®-naphthol methyl ether, nerol, nitrobenzene, n-nonylaldehyde, nonyl alcohol, n-octylaldehyde, p-oxyacetophenone, pentadecanolide, ®-phenylethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, ©-undelactone, vanillin, veratrumaldehyde, cinnamaldehyde, cinnamyl alcohol, cinnamic acid, cinnamic acid ethyl ester, cinnamic acid benzyl ester. Included among the more-volatile scents are, in particular, the lower-boiling fragrances of natural or synthetic origin, which can be used alone or in mixtures. Examples of more-volatile scents are alkylisothiocyanates (alkyl mustard oils), butanedione, limonene, linalool, linalyl acetate and propionate, menthol, menthone, methyl-n-heptenone, phellandrene, phenylacetaldehyde, terpinyl acetate, citral, citronellal.

According to a further preferred embodiment, the agent according to the present invention (i.e. washing or cleaning agent, cosmetic agent, or air freshening agent) comprises at least one, by preference multiple, active components, in particular cosmetic components or components having washing, care-providing, or cleaning activity, advantageously selected from the group encompassing anionic surfactants, cationic surfactants, amphoteric surfactants, nonionic surfactants, acidifying agents, alkalizing agents, anti-creasing compounds, antibacterial substances, antioxidants, antiredeposition agents, antistatic agents, builder substances, bleaching agents, bleach activators, bleach stabilizers, bleach catalysts, ironing adjuvants, cobuilders, scents, shrinkage preventers, electrolytes, enzymes, color protectants, coloring agents, dyes, color transfer inhibitors, fluorescent agents, fungicides, germicides, odor-complexing substances, adjuvants, hydrotropes, rinse aids, complexing agents, preservatives, corrosion inhibitors, water-miscible organic solvents, optical brighteners, perfumes, perfume carriers, luster agents, pH adjusting agents, proofing and impregnation agents, polymers, swelling and anti-slip agents, foam inhibitors, sheet silicates, dirt-repelling substances, silver protectants, silicone oils, soil release active substances, UV protection substances, viscosity regulators, thickening agents, discoloration inhibitors, anti-gray agents, vitamins, and/or fabric softeners. For purposes of this invention, indications for the agent according to the present invention in wt % refer, unless otherwise indicated, to the total weight of the agent according to the present invention.

The quantities of the individual ingredients in the agents according to the present invention (i.e. washing or cleaning agent, cosmetic agent, or air freshening agent) are aimed in each case toward the intended use of the relevant agent, and the skilled artisan is familiar in principle with the orders of magnitude of the quantities of ingredients to be used, or can gather them from the relevant technical literature. The surfactant content, for example, will be selected to be higher or lower depending on the intended use of the agents according to the present invention. For example, the surfactant content of, for example, washing agents can usually be equal to between 10 and 50 wt %, by preference between 12.5 and 30 wt %, and in particular between 15 and 25 wt %, while, for example, cleaning agents for automatic dishwashing can contain, for example, between 0.1 and 10 wt %, by preference between 0.5 and 7.5 wt %, and in particular between 1 and 5 wt % surfactants.

The agents according to the present invention (i.e. washing or cleaning agents, cosmetic agents, or air freshening agents) can contain surfactants; anionic surfactants, nonionic surfactants, and mixtures thereof, but also cationic surfactants, are preferably appropriate. Suitable nonionic surfactants are, in particular, ethoxylation and/or propoxylation products of alkyl glycosides and/or of linear or branched alcohols each having 12 to 18 carbon atoms in the alkyl portion and 3 to 20, by preference 4 to 10, alkyl ether groups. Also usable are corresponding ethoxylation and/or propoxylation products of N-alkylamines, vicinal diols, fatty acid esters and fatty acid amides that correspond, in terms of the alkyl portion, to the aforesaid long-chain alcohol derivatives, and of alkylphenols having 5 to 12 carbon atoms in the alkyl residue.

Suitable anionic surfactants are, in particular, soaps, and those that contain sulfate or sulfonate groups having preferably alkali ions as cations. Usable soaps are preferably the alkali salts of the saturated or unsaturated fatty acids having 12 to 18 carbon atoms. Such fatty acids can also be used in incompletely neutralized form. Included among the usable surfactants of the sulfate type are the salts of the sulfuric acid semiesters of fatty alcohols having 12 to 18 carbon atoms, and the sulfatization products of the aforesaid nonionic surfactants having a low degree of ethoxylation. Included among the usable surfactants of the sulfonate type are linear alkylbenzenesulfonates having 9 to 14 carbon atoms in the alkyl portion, alkanesulfonates having 12 to 18 carbon atoms, and olefinsulfonates having 12 to 18 carbon atoms that are produced upon reaction of corresponding monoolefins with sulfur trioxide, as well as alpha-sulfofatty acid esters that are produced upon sulfonation of fatty acid methyl or ethyl esters.

Cationic surfactants are by preference selected from among the esterquats and/or the quaternary ammonium compounds (QACs) in accordance with the general formula $(R^{I})(R^{II})(R^{III})(R^{IV})N^{+} X^{-}$, in which $R^{I}$ to $R^{IV}$ denote identical or different $C_{1-22}$ alkyl residues, $C_{7-28}$ aralkyl residues, or heterocyclic residues, such that two (or in the case of an aromatic bond such as in pyridine, even three) residues form, together with the nitrogen atom, the heterocycle (e.g. a pyridinium or imidazolinium compound), and $X^{-}$ denotes halide ions, sulfate ions, hydroxide ions, or similar anions. QACs can be manufactured by the reaction of tertiary amines with alkylating agents such as, for example, methyl chloride, benzyl chloride, dimethyl sulfate, dodecyl bromide, but also ethylene oxide. The alkylation of tertiary amines having a long alkyl residue and two methyl groups can be achieved particularly easily, and the quaternization of tertiary amines having two long residues and one methyl group can also be carried out using methyl chloride under mild conditions. Amines that possess three long alkyl residues or hydroxy-substituted alkyl residues have low reactivity, and are quaternized, for example, using dimethyl sulfate. Suitable QACs are, for example, benzalkonium chloride (N-alkyl-N,N-dimethylbenzylammonium chloride), benzalkon B (m,p-dichlorobenzyldimethyl-$C_{12}$-alkylammonium chloride), benzoxonium chloride (benzyldodecyl-bis(2-hydroxyethyl)ammonium chloride), cetrimonium bromide (N-hexadecyl-N,N-trimethylammonium bromide), benzetonium chloride (N,N-dimethyl-N-[2-[2-[p-(1,1,3,3-tetramethylbutyl)phenoxy]ethoxy]ethyl]benzylammonium chloride), dialkyldimethylammonium chlorides such as di-n-decyldimethylammonium chloride, didecyldimethylammonium bromide, dioctyldimethylammonium chloride, 1-cetylpyridinium chloride, and thiazoline iodide, as well as mixtures thereof. Preferred QACs are the benzalkonium chlorides having $C_8$ to $C_{22}$ alkyl residues, in particular $C_{12}$ to $C_{14}$ alkylbenzyldimethylammonium chloride.

Preferred esterquats are methyl-N-(2-hydroxyethyl)-N,N-di(tallowacyloxyethyl)ammonium methosulfate, bis(palmitoyloxyethyl)hydroxyethylmethylammonium methosulfate, or methyl-N,N-bis(acyloxyethyl)-N-(2-hydroxyethyl)ammonium methosulfate. Commercially usual examples are the methylhydroxyalkyldialkoyloxyalkylammonium methosulfates marketed by the Stepan company under the Stepantex® trademark, or the products of Cognis Deutschland GmbH known under the trade name Dehyquart® resp. the products of the manufacturer Goldschmidt-Wilco known under the name Rewoquat®.

Surfactants are contained in the agents according to the present invention (i.e. washing or cleaning agent, cosmetic agent, or air freshening agent) in quantitative proportions by preference from 5 wt % to 50 wt %, in particular from 8 wt % to 30 wt %. In laundry post-treatment agents in particular, by preference up to 30 wt %, in particular 5 wt % to 15 wt % surfactants are used, among them preferably cationic surfactants at least in part.

An agent according to the present invention, in particular a washing or cleaning agent, by preference contains at least one water-soluble and/or water-insoluble, organic and/or inorganic builder. Included among the water-soluble organic builder substances are polycarboxylic acids, in particular citric acid and sugar acids, monomeric and polymeric aminopolycarboxylic acids, in particular methylglycinediacetic acid, nitrilotriacetic acid, and ethylenediaminetetraacetic acid, as well as polyaspartic acid, polyphosphonic acids, in particular aminotris(methylenephosphonic acid), ethylenediaminetetrakis(methylenephosphonic acid), and 1-hydroxyethane-1,1-diphosphonic acid, polymeric hydroxy compounds such as dextrin, as well as polymeric (poly)carboxylic acids, polymeric acrylic acids, methacrylic acids, maleic acids, and mixed polymers thereof, which can also contain, polymerized into them, small proportions of polymerizable substances having no carboxylic-acid functionality. Suitable (although less preferred) compounds of this class are copolymers of acrylic acid or methacrylic acid with vinyl ethers, such as vinyl methyl ethers, vinyl esters, ethylene, propylene, and styrene, in which the proportion of acid is equal to at least 50 wt %. Especially for the manufacture of liquid detergents, the organic builder substances can be used in the form of aqueous solutions, by preference in the form of 30- to 50-weight-percent aqueous solutions. All the aforesaid acids are used as a rule in the form of their water-soluble salts, in particular their alkali salts.

Organic builder substances can be contained if desired in quantities of up to 40 wt %, in particular up to 25 wt %, and by preference from 1 wt % to 8 wt %. Quantities close to the aforesaid upper limit are used by preference in pasty or liquid, in particular water-containing, agents according to the present invention. Laundry post-treatment agents, for example fabric softeners, according to the present invention can also, if applicable, be free of organic builder.

Possibilities as water-soluble inorganic builder materials are, in particular, alkali silicates and polyphosphates, by preference sodium triphosphate. Crystalline or amorphous alkali aluminosilicates can be used in particular as water-insoluble, water-dispersible inorganic builder materials, if desired, in quantities of e.g. up to 50 wt %, by preference not above 40 wt %, and in liquid agents in particular from 1 wt % to 5 wt %. Among these, the crystalline sodium aluminosilicates of washing-agent quality, in particular zeolite A, P, and if applicable X, are preferred. Quantities close to the aforesaid upper limit are used by preference in solid, particulate agents. Suitable aluminosilicates comprise, in particular, no particles having a particle size greater than 30 μm, and by preference are made up at a proportion of at least 80 wt % of particles having a size less than 10 μm.

Suitable substitutes respectively partial substitutes for the aforesaid aluminosilicate are crystalline alkali silicates, which can be present alone or mixed with amorphous silicates. The alkali silicates usable in the agents according to the present invention as builders have by preference a molar ratio of alkali oxide to $SiO_2$ below 0.95, in particular from 1:1.1 to 1:12, and can be present in amorphous or crystalline fashion. Preferred alkali silicates are the sodium silicates, in particular the amorphous sodium silicates, having a $Na_2O:SiO_2$ molar ratio from 1:2 to 1:2.8. Crystalline sheet silicates of the general formula $Na_2Si_xO_{2x+1} \cdot yH_2O$, in which x, the so-called modulus, is a number from 1.9 to 4 and y is a number from 0 to 20, and preferred values for x are 2, 3, or 4, are preferred for use as crystalline silicates, which can be present alone or in a mixture with amorphous silicates. Preferred crystalline sheet silicates are those in which x in the general formula recited assumes the values 2 or 3. In particular, both ®- and ™-sodium disilicates ($Na_2Si_2O_5 \cdot yH_2O$) are preferred. Practically anhydrous crystalline alkali silicates manufactured from amorphous alkali silicates and having the aforesaid general formula, in which x denotes a number from 1.9 to 2.1, can also be used in agents according to the present invention. In a further preferred embodiment of agents according to the present invention, a crystalline sodium sheet silicate having a modulus from 2 to 3 can be used, such as the one that can be manufactured from sand and soda. Crystalline sodium silicates having a modulus in the range from 1.9 to 3.5 are used in a further preferred embodiment of agents according to the present invention. If alkali aluminosilicate, in particular zeolite, is present as an additional builder substance, the weight ratio of aluminosilicate to silicate, based in each case on anhydrous active substances, is equal to 1:10 to 10:1. In agents that contain both amorphous and crystalline alkali silicates, the weight ratio of amorphous alkali silicate to crystalline alkali silicate is by preference equal to 1:2 to 2:1, and in particular 1:1 to 2:1.

Builder substances are contained in the washing agents according to the present invention, if desired, by preference in quantities of up to 60 wt %, in particular from 5 wt % to 40 wt %. Laundry post-treatment agents according to the present invention, for example fabric softeners, according to the present invention are by preference free of inorganic builders.

Peroxygen compounds that are suitable are, in particular, organic peracids respectively peracid salts of organic acids such as phthalimidopercapronic acid, perbenzoic acid, or salts of diperdodecanedioic acid, hydrogen peroxide, and inorganic salts that release hydrogen peroxide under application conditions, such as perborate, percarbonate, and/or persilicate. If solid peroxygen compounds are to be used, they can be utilized in the form of powders or granulates, which in principle can also be encased in known fashion. Alkali percarbonate, alkali perborate monohydrate, or (in particular in liquid agents) hydrogen peroxide in the form of aqueous solutions that contain 3 wt % to 10 wt % hydrogen peroxide, are used with particular preference. If a washing agent according to the present invention contains bleaching agents, such as preferably peroxygen compounds, the latter are present in quantities of preferably up to 50 wt %, in particular from 5 wt % to 30 wt %. The addition of small quantities of known bleaching-agent stabilizers, for example phosphonates, borates resp. metaborates, and metasilicates, as well as magnesium salts such as magnesium sulfate, may be useful.

Compounds that, under perhydrolysis conditions, yield aliphatic peroxocarboxylic acids having preferably 1 to 10 carbon atoms, in particular 2 to 4 carbon atoms, and/or (optionally substituted) perbenzoic acid, can be used as bleach activators. Substances that carry the O- and/or N-acyl groups having the aforesaid number of carbon atoms, and/or optionally substituted benzoyl groups, are suitable. Multiply acylated alkylenediamines, in particular tetraacetylethylendiamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenolsulfonates, in particular n-nonanoyl or isononanoyl oxybenzenesulfonate (n- or iso-NOBS), carboxylic acid anhydrides, in particular phthalic acid anhydride, acylated polyvalent alcohols, in particular triacetin, ethylene glycol diacetate, 2,5-diacetoxy-2,5-dihydrofuran, and enol esters, as well as acetylated sorbitol and mannitol respectively mixtures thereof (SORMAN), acylated sugar derivatives, in particular pentaacetylglucose (PAG), pentaacetylfructose, tetraacetylxylose and octaacetyllactose, as well as acetylated, optionally N-alkylated glucamine and gluconolactone, and/or N-acylated lactams, for example N-benzoylcaprolactam, are preferred. Hydrophilically substituted acyl acetates and acyl lactams are likewise used in preferred fashion. Combinations of conventional bleach activators can also be used. Such bleach activators can be contained in the usual quantity range, by preference in quantities from 1 wt % to 10 wt %, in particular 2 wt % to 8 wt %, based on the total agent.

In addition to or instead of the aforementioned conventional bleach activators, sulfonimines and/or bleach-intensifying transition metal salts respectively transition metal complexes can also be contained as so-called bleach catalysts.

Suitable enzymes usable in the agents are those from the class of the proteases, cutinases, amylases, pullulanases, hemicellulases, cellulases, lipases, oxidases, and peroxidases, as well as mixtures thereof. Enzymatic active substances recovered from fungi or bacteria, such as *Bacillus subtilis, Bacillus licheniformis, Streptomyces griseus, Humicola lanuginosa, Humicola insolens, Pseudomonas pseudoalcaligenes*, or *Pseudomonas cepacia*, are particularly suitable. The enzymes that are used as applicable can be adsorbed onto carrier substances and/or embedded into encasing substances in order to protect them from premature inactivation. They are contained in the washing agents according to the present invention, if desired, by preference in quantities not above 5 wt %, in particular from 0.2 wt % to 2 wt %.

The agents can optionally contain as optical brighteners, for example, derivatives of diaminostilbenedisulfonic acid resp. alkali metal salts thereof. Suitable, for example, are salts of 4,4'-bis(2-anilino-4-morpholino-1,3,5-triazinyl-6-amino) stilbene-2,2'-disulfonic acid, or compounds of similar structure that carry, instead of the morpholino group, a diethanolamino group, a methylamino group, an anilino group, or a 2-methoxyethylamino group.

Included among the suitable foam inhibitors are, for example, organopolysiloxanes and mixtures thereof with microfine, optionally silanated silicic acid, as well as paraffin waxes and mixtures thereof with silanated silicic acid or bis-fatty acid alkylenediamides. Mixtures of different foam inhibitors, for example those made of silicones, paraffins, or waxes, are also used with advantage. The foam inhibitors, in particular silicone- and/or paraffin-containing foam inhibitors, are by preference bound to a granular carrier substance that is soluble respectively dispersible in water. Mixtures of paraffins and bistearylethylenediamides are particularly preferred in this context.

In addition, the agents can also contain components that positively influence the ability of oils and fats to be washed out of textiles (so-called "soil release active substances"). This effect becomes particularly apparent when the soiled textile is one that has already been previously washed several times with an agent according to the present invention that contains this oil- and fat-releasing component. The preferred oil- and fat-releasing components include, for example, non-ionic cellulose ethers such as methyl cellulose and methylhydroxypropyl cellulose having a 15 to 30 wt % proportion of methoxy groups and a 1 to 15 wt % proportion of hydroxypropoxyl groups, based in each case on the nonionic cellulose ethers, as well as polymers, known from the existing art, of phthalic acid and/or terephthalic acid resp. of their derivatives with monomeric and/or polymeric diols, in particular polymers of ethylene terephthalates and/or polyethylene glycol terephthalates or anionically and/or nonionically modified derivatives thereof.

The agents can also contain color transfer inhibitors, by preference in quantities from 0.1 wt % to 2 wt %, in particular 0.1 wt % to 1 wt %, which in a preferred embodiment of the invention are polymers of vinylpyrrolidone, vinylimidazole, vinylpyridine-N-oxide, or copolymers thereof.

The purpose of anti-gray agents is to keep dirt that has been detached from the textile fibers suspended in the bath. Water-soluble colloids, usually organic in nature, are suitable for this, for example starch, size, gelatin, salts of ethercarboxylic or ethersulfonic acids of starch or of cellulose, or salts of acid sulfuric acid esters of cellulose or of starch. Water-soluble polyamides containing acid groups are also suitable for this purpose. Starch derivatives other than those recited above can also be used, for example aldehyde starches. Cellulose ethers such as carboxymethyl cellulose (sodium salt), methyl cellulose, hydroxyalkyl cellulose, and mixed ethers such as methylhydroxyethyl cellulose, methylhydroxypropyl cellulose, methylcarboxymethyl cellulose, and mixtures thereof are preferably used, for example in quantities from 0.1 to 5 wt % based on the agent.

Included among the organic solvents usable in the agents according to the present invention, especially when the latter exist in liquid or pasty form, are alcohols having 1 to 4 carbon atoms, in particular methanol, ethanol, isopropanol, and tert-butanol, diols having 2 to 4 carbon atoms, in particular ethylene glycol and propylene glycol, as well as mixtures thereof, and the ethers derivable from the aforesaid compound classes. Water-miscible solvents of this kind are present in the agents according to the present invention by preference in quantities not above 30 wt %, in particular from 6 wt % to 20 wt %.

In order to establish a desired pH that does not result of itself from mixture of the other components, the agents according to the present invention can contain system-compatible and environmentally compatible acids, in particular citric acid, acetic acid, tartaric acid, malic acid, lactic acid, glycolic acid, succinic acid, glutaric acid, and/or adipic acid, but also mineral acids, in particular sulfuric acid, or bases, in particular ammonium hydroxides or alkali hydroxides. pH regulators of this kind are optionally contained in the agents according to the present invention in quantities by preference not above 20 wt %, in particular from 1.2 wt % to 17 wt %.

The manufacture of solid agents according to the present invention (i.e. in particular washing or cleaning agents) presents no difficulties and can in principle occur in known fashion, for example by spray-drying or granulation; an optional peroxygen compound and optional bleach catalyst can, if applicable, be added later. A method comprising an extrusion step is preferred for the manufacture of agents according to the present invention having an elevated bulk weight, in particular in the range from 650 g/l to 950 g/l. The manufacture of liquid agents according to the present invention likewise presents no difficulties and can likewise occur in known fashion.

Manufacture of the ketones according to the present invention is described in exemplifying fashion in the Examples section, with reference to the manufacture of a scent storage substance containing δ-damascones. The other ketones of the general formula (I), and in particular all ketones of formulas (VI) to (XXV), are also accessible via the principle of this synthesis route.

According to a preferred embodiment, the teaching according to the present invention can be used to significantly reduce the perfume proportion in washing, cleaning, and toiletry agents. As a result, it is possible to offer perfumed products even for those particularly sensitive consumers who, because of specific incompatibilities and irritations, can use normally perfumed products only to a limited extent or not at all.

A preferred solid, in particular powdered, washing agent according to the present invention can in particular also contain, alongside the ketone according to the present invention, components that are selected, for example, from the following:

- anionic surfactants such as, by preference, alkylbenzenesulfonate, alkyl sulfate, e.g. in quantities by preference from 5 to 30 wt %,
- nonionic surfactants such as, by preference, fatty alcohol polyglycol ethers, alkylpolyglucoside, fatty acid glucamide, e.g. in quantities by preference from 0.5 to 15 wt %,
- builders such as, for example, zeolite, polycarboxylate, sodium citrate, in quantities from, for example, 0 to 70 wt %, advantageously 5 to 60 wt %, by preference 10 to 55 wt %, in particular 15 to 40 wt %,
- alkalis such as, for example, sodium carbonate, in quantities e.g. from 0 to 35 wt %, advantageously 1 to 30 wt %, by preference 2 to 25 wt %, in particular 5 to 20 wt %,
- bleaching agents such as, for example, sodium perborate, sodium percarbonate, in quantities e.g. from 0 to 30 wt %, advantageously 5 to 25 wt %, by preference 10 to 20 wt %,
- corrosion inhibitors, e.g. sodium silicate, in quantities e.g. from 0 to 10 wt %, advantageously 1 to 6 wt %, by preference 2 to 5 wt %, in particular 3 to 4 wt %,
- stabilizers, e.g. phosphonates, advantageously 0 to 1 wt %,
- foam inhibitor, e.g. soap, silicone oils, paraffins, advantageously 0 to 4 wt %, by preference 0.1 to 3 wt %, in particular 0.2 to 1 wt %,
- enzymes, e.g. proteases, amylases, cellulases, lipases, advantageously 0 to 2 wt %, by preference 0.2 to 1 wt %, in particular 0.3 to 0.8 wt %,
- anti-gray agent, e.g. carboxymethyl cellulose, advantageously 0 to 1 wt %,
- discoloration inhibitor, e.g. polyvinylpyrrolidone derivatives, advantageously 0 to 2 wt %,
- adjusting agent, e.g. sodium sulfate, advantageously 0 to 20 wt %,
- optical brightener, e.g. stilbene derivative, biphenyl derivative, advantageously 0 to 0.4 wt %, in particular 0.1 to 0.3 wt %,
- optionally further fragrances,
- optionally water,
- optionally soap,
- optionally bleach activators,
- optionally cellulose derivatives,
- optionally dirt repellents, "wt %" being based in each case on the total agent.

In another preferred embodiment of the invention, the agent is present in liquid form, by preference in gel form. Preferred liquid washing or cleaning agents, as well as cosmetics, have water contents of, for example, 10 to 95 wt %, by preference 20 to 80 wt %, and in particular 30 to 70 wt %, based on the total agent. In the case of liquid concentrates the water content can also be particularly low, e.g. <30 wt %, by preference <20 wt %, in particular <15 wt %, "wt %" being based in each case on the total agent. The liquid agents can also contain non-aqueous solvents.

A preferred liquid, in particular gel-type, washing agent according to the present invention can in particular also contain, alongside the ketone according to the present invention, components that are selected e.g. from the following:

- anionic surfactants such as, by preference, alkylbenzenesulfonate, alkyl sulfate, e.g. in quantities by preference from 5 to 40 wt %,
- nonionic surfactants such as, by preference, fatty alcohol polyglycol ethers, alkylpolyglucoside, fatty acid glucamide, for example in quantities by preference from 0.5 to 25 wt %,
- builders such as, for example, zeolite, polycarboxylate, sodium citrate, advantageously 0 to 15 wt %, by preference 0.01 to 10 wt %, in particular 0.1 to 5 wt %,
- foam inhibitor, e.g. soap, silicone oils, paraffins, in quantities e.g. from 0 to 10 wt %, advantageously 0.1 to 4 wt %, by preference 0.2 to 2 wt %, in particular 1 to 3 wt %,
- enzymes, e.g. proteases, amylases, cellulases, lipases, in quantities e.g. from 0 to 3 wt %, advantageously 0.1 to 2 wt %, by preference 0.2 to 1 wt %, in particular 0.3 to 0.8 wt %,
- optical brightener, e.g. stilbene derivative, biphenyl derivative, in quantities e.g. from 0 to 1 wt %, advantageously 0.1 to 0.3 wt %, in particular 0.1 to 0.4 wt %,
- optionally further fragrances,
- optionally stabilizers,
- water,
- optionally soap, in quantities e.g. from 0 to 25 wt %, advantageously 1 to 20 wt %, by preference 2 to 15 wt %, in particular 5 to 10 wt %,
- optionally solvents (by preference alcohols), advantageously 0 to 25 wt %, by preference 1 to 20 wt %, in particular 2 to 15 wt %, "wt %" being based in each case on the total agent.

A preferred liquid fabric softener according to the present invention can in particular also contain, alongside the ketone according to the present invention, components that are selected from the following:

- cationic surfactants, such as especially esterquats, e.g. in quantities from 5 to 30 wt %,
- cosurfactants such as, for example, glycerol monostearate, stearic acid, fatty alcohols, fatty alcohol ethoxylates, e.g. in quantities from 0 to 5 wt %, by preference 0.1 to 4 wt %,
- emulsifiers such as, for example, fatty amine ethoxylates, e.g. in quantities from 0 to 4 wt %, by preference 0.1 to 3 wt %,
- optionally further scents,
- dyes, by preference in the ppm range,
- stabilizers, by preference in the ppm range,
- solvents such as, in particular, water, in quantities by preference from 60 to 90 wt %, "wt %" being based in each case on the total agent.

A further subject of the invention is a method for long-lasting scenting of surfaces, a ketone according to one of formulas (I) to (XXV), or a washing or cleaning agent according to the present invention, being applied onto the surface to be scented (e.g. textile, tableware, floor), and said surface then being exposed to an electromagnetic radiation encompassing the wavelengths from 200 to 400 nm.

A further subject of the invention is a method for long-lasting room scenting, an air freshening agent according to the present invention being exposed to an electromagnetic radiation encompassing the wavelengths from 200 to 400 nm.

EXAMPLE

Preparation of a ketone of the general formula (I):

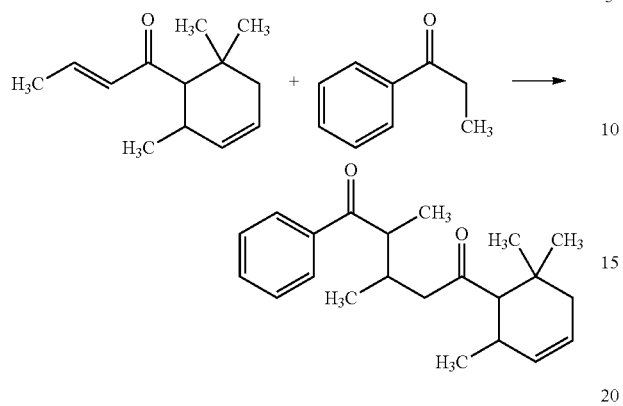

Under nitrogen, 8.50 g diisopropylamine was prepared in 210 ml THF, and the solution was cooled to −78° C. This was followed by the addition of 11.3 g propiophenone, and then the addition of 40.3 ml of a butyl lithium solution (2.5 molar in hexane; corresponds to 100.8 mmol). The reaction solution was stirred for 1 hour at −78° C. This was followed by the addition, while stirring, of 24 g dried cerium chloride (cerium (III) chloride, dried; corresponds to 98 mmol; manufactured from: cerium (III) chloride*7 H$_2$O by drying for six hours at 150° C. under high vacuum). The reaction solution was then stirred for 30 minutes at −78° C. 14.8 g δ-damascone was then slowly dripped in using a dropping funnel, and the reaction solution was stirred further at −78° C. Cooling was then discontinued, and addition of a saturated ammonium chloride solution occurred at approx. −10° C. For purification, extraction was performed three times using 350 ml ether each time, and the resulting light-yellow organic phase was then extracted with shaking with water, later with a saturated NaCl solution. The organic phase was then dried over magnesium sulfate. Solvent was removed from the filtrate at reduced pressure. Lastly, the resulting crude product was distilled under high vacuum, yielding the desired target product in a quantity of 29 g.

The ketone manufactured in this fashion exhibited a very good scenting effect when used in washing agents and fabric softeners for textile treatment. In particular, a better persistence of the scent impression on the laundry washed therewith, and then dried, was found, as compared with washing agents and fabric softeners that contained an equivalent quantity of δ-damascone but were otherwise equivalent. The fresh scent impression of the textiles persisted appreciably longer, both after line drying and, in particular, after drying in an automatic dryer.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A ketone selected from the group of ketones corresponding to formula, (III), (IV), or formula (V)

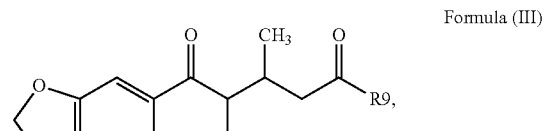

Formula (III)

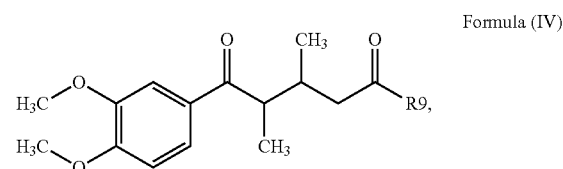

Formula (IV)

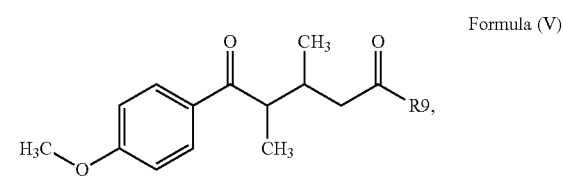

Formula (V)

where the residue R9 denotes a hydrocarbon residue having at least 5 carbon atoms.

2. A ketone selected from the group of ketones corresponding to one of the following formulas (VI) to (XXV)

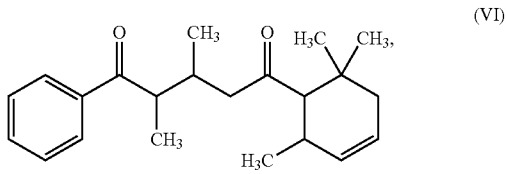

(VI)

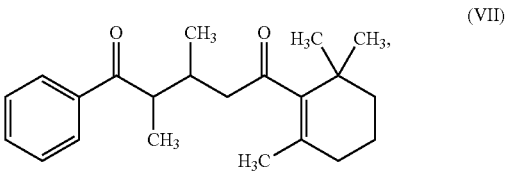

(VII)

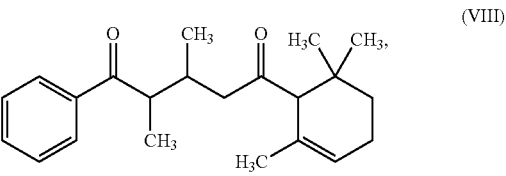

(VIII)

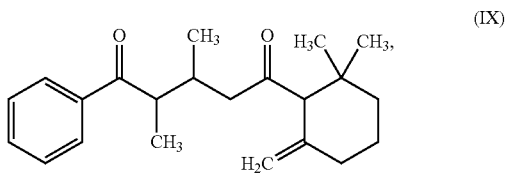

(IX)

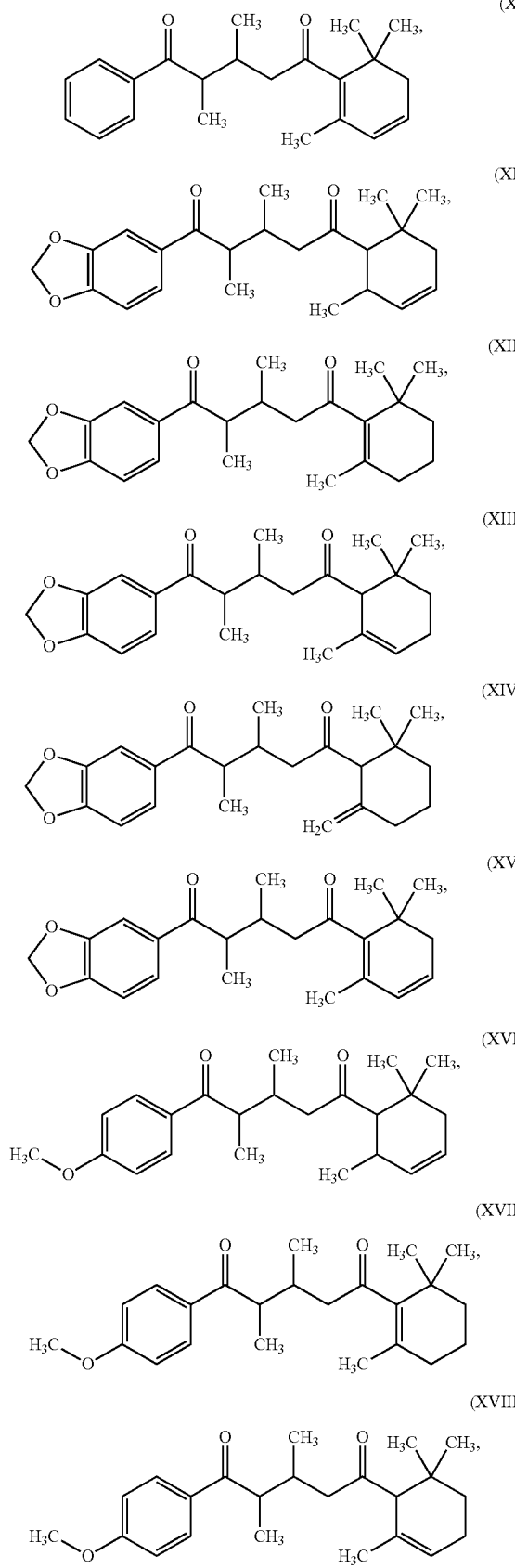
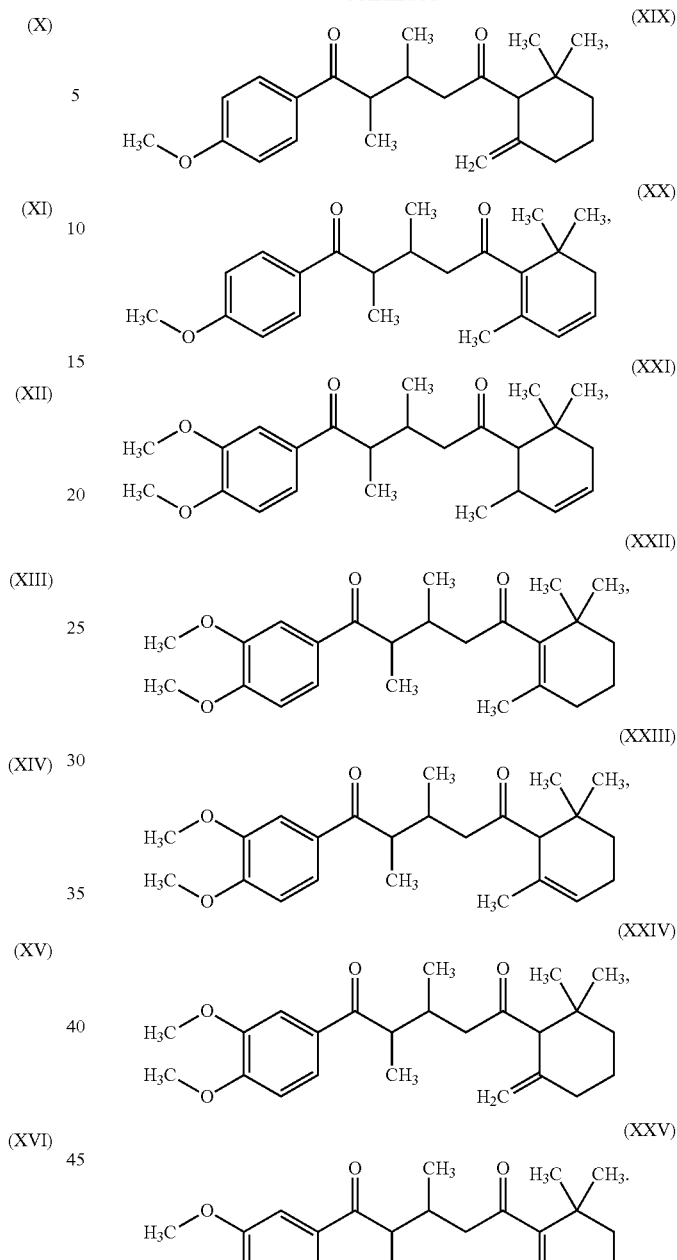

3. A washing or cleaning agent containing at least one ketone according to claim 1, said ketone being contained in quantities between 0.0001 and 5 wt % based in on the total agent.

4. The washing or cleaning agent according to claim 3, wherein it contains at least one surfactant selected from the group consisting of anionic, cationic, nonionic, zwitterionic, amphoteric surfactants or mixtures thereof.

5. The washing or cleaning agent according to one of claims 3, wherein it is present in solid or liquid form.

6. An air freshening agent containing at least one ketone according to claim 1, said ketone being contained in quantities between 0.0001 and 50 wt % based on the total agent.

7. A method for long-lasting scenting of surfaces, wherein a ketone according to claim 1 is applied onto the surface to be scented, and said surface is then exposed to an electromagnetic radiation encompassing the wavelengths from 200 to 400 nm.

8. A washing or cleaning agent containing at least one ketone according to claim 2, said ketone being contained in quantities between 0.0001 and 5 wt % based in on the total agent.

9. The washing or cleaning agent according to claim 8, wherein it contains at least one surfactant selected from the group consisting of anionic, cationic, nonionic, zwitterionic, amphoteric surfactants or mixtures thereof.

10. An air freshening agent containing at least one ketone according claim 2, said ketone being contained in quantities between 0.0001 and 50 wt % based on the total agent.

* * * * *